US00PP31504P3

(12) United States Plant Patent
Maillard et al.

(10) Patent No.: US PP31,504 P3
(45) Date of Patent: Mar. 3, 2020

(54) NECTARINE TREE NAMED 'NSRED15270'

(50) Latin Name: ***Prunus persica* (L.) Batsch**
Varietal Denomination: NSRED15270

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,466

(22) Filed: Nov. 20, 2018

(65) Prior Publication Data

US 2019/0159387 P1 May 23, 2019

(30) Foreign Application Priority Data

Nov. 23, 2017 (QZ) ..... PBR 2017/3058

(51) Int. Cl.
*A01H 5/08* (2018.01)
*A01H 6/74* (2018.01)

(52) U.S. Cl.
USPC ..... Plt./187
CPC ..... *A01H 6/7454* (2018.05)

(58) Field of Classification Search
USPC ..... Plt./187
CPC ..... A01H 5/0856
See application file for complete search history.

*Primary Examiner* — Kent L Bell
(74) *Attorney, Agent, or Firm* — Birch, Stewart, Kolasch & Birch, LLP

(57) ABSTRACT

A new and distinct variety of red blood nectarine tree denominated 'NSRED15270' has fruits with high eating quality and very long shelf life without alteration before and after harvesting, with a semi-sweet red blood colored flesh, and a very high percentage of dark purple red blush on skin surface.

3 Drawing Sheets

Botanical classification: *Prunus persica* (L.) Batsch.

Variety denomination: 'NSRED15270'.

This application claims priority of Community plant variety right No. 2017/3058 filed on Nov. 23, 2017 (Nov. 23, 2017) which is hereby incorporated by reference in its entirety.

BACKGROUND OF THE NEW VARIETY

The present invention relates to a new and distinct variety of blood nectarine tree, also named red colored flesh nectarine, *Prunus persica* (L.) Batsch, which has been given the variety denomination 'NSRED15270'. This new tree produces fruits with a long shelf life without alteration both on the tree after growth completion and after harvesting, very good eating quality, semi clingstone dark red or blood red flesh fruits for fresh market in August in the Pyrénées-Orientales department, France. Contrast is made to 'NECTARPERF' white nectarine tree (U.S. Plant Pat. No. 23,357) for reliable description. 'NSRED15270' is a promising candidate for commercial success in that it has very attractive fruits with very long shelf life without alteration both before and after harvesting.

ORIGIN OF THE VARIETY

The 'NSRED15270' red nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 700 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'NSRED15270' variety resulted from an open pollination of the 'NECTARPERF' white nectarine tree (U.S. Plant Pat. No. 23,357), which was used as the seed parent. Then, the pollen parent of the new variety 'NSRED15270' remains unknown.

The 'NSRED15270' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NSRED15270' red nectarine tree blooms during March near Elne in the Pyrénées- Orientales department, France. More particularly, it usually blooms between March 6$^{th}$ and March 21$^{st}$. The blooming period is considered medium. However, it was observed that its date of blooming seems to be highly dependant on climatic conditions.

The first fruit of 'NSRED15270' ripens generally at the end of July. More particularly, it usually ripens between July 24$^{th}$ and August 4$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
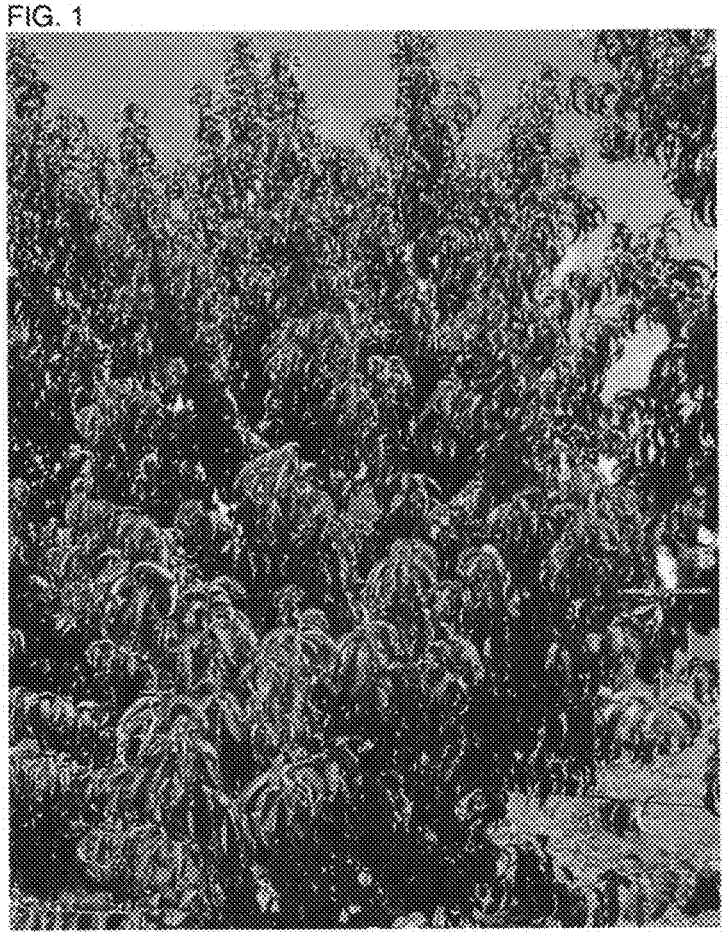
FIG. 1 is a color photograph which shows a view of a tree of the new variety in orchard, with branches bearing fruits.
Figure 2:
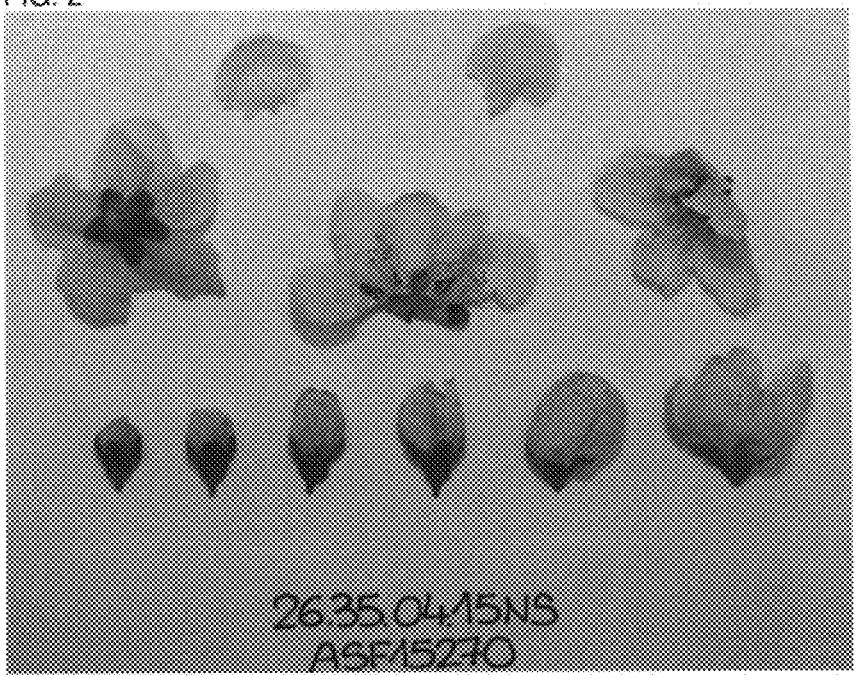
FIG. 2 is a color photograph which depicts the flower buds at different development stages, and the reverse and side view of the flower and the reproductive organs with petals removed, of the new variety.
Figure 3:
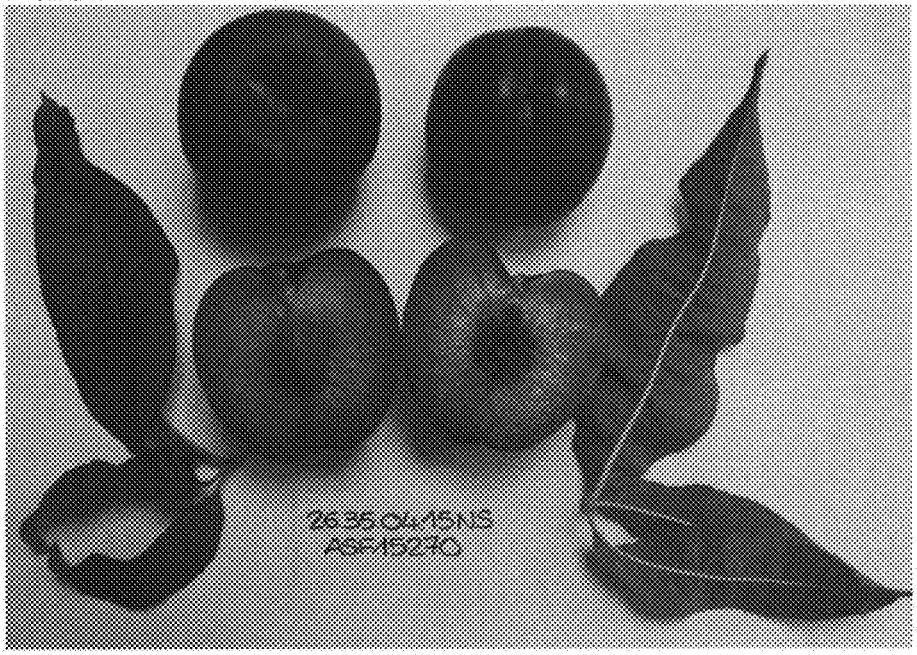
FIG. 3 is a color photograph which shows the upper and lower sides of leaves of the variety and three typical specimens of the fruit, one having been cut in halves with the stone being left into one of the halves for depicting fruit flesh stone and stone cavity of the new variety.
Figure 4:
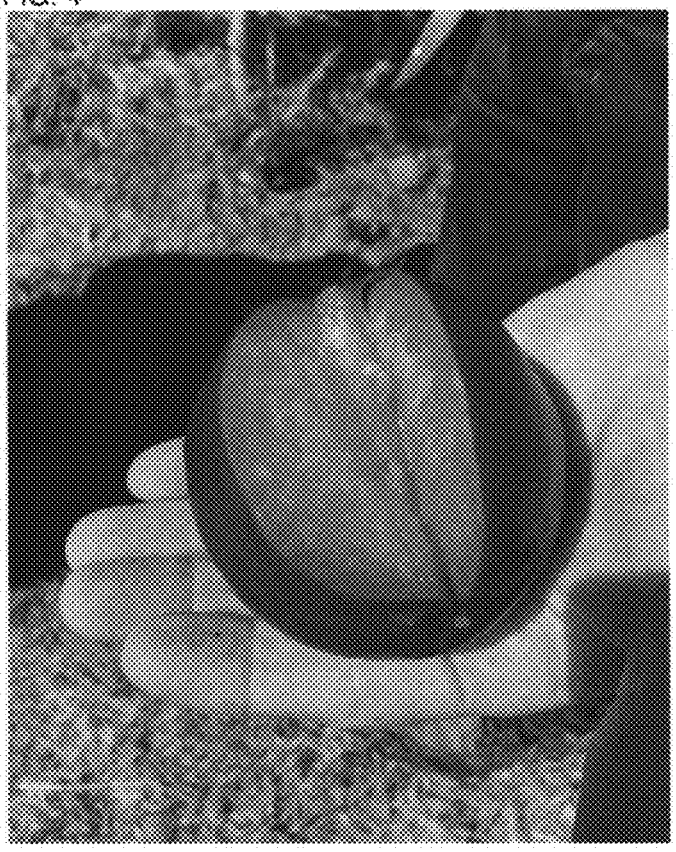
FIG. 4 is a color photograph that shows a close view of one typical fruit of the new variety 'NSRED15270' at ripening time, a quarter of the fruit having been removed to show the fruit flesh.
Figure 5:
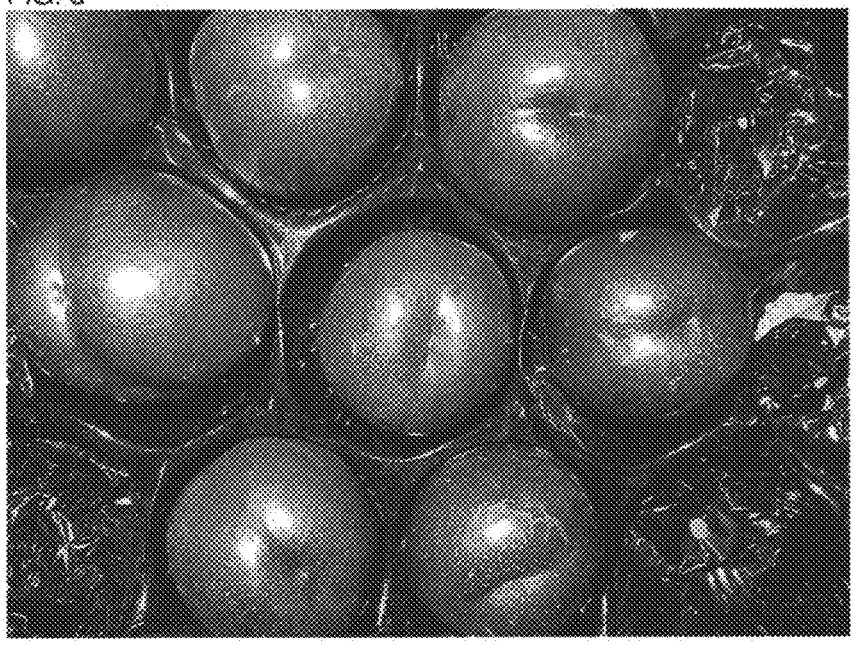
FIG. 5 is a color photograph that shows a close view of typical fruits of the new variety 'NSRED15270' at ripening time
Figure 6:
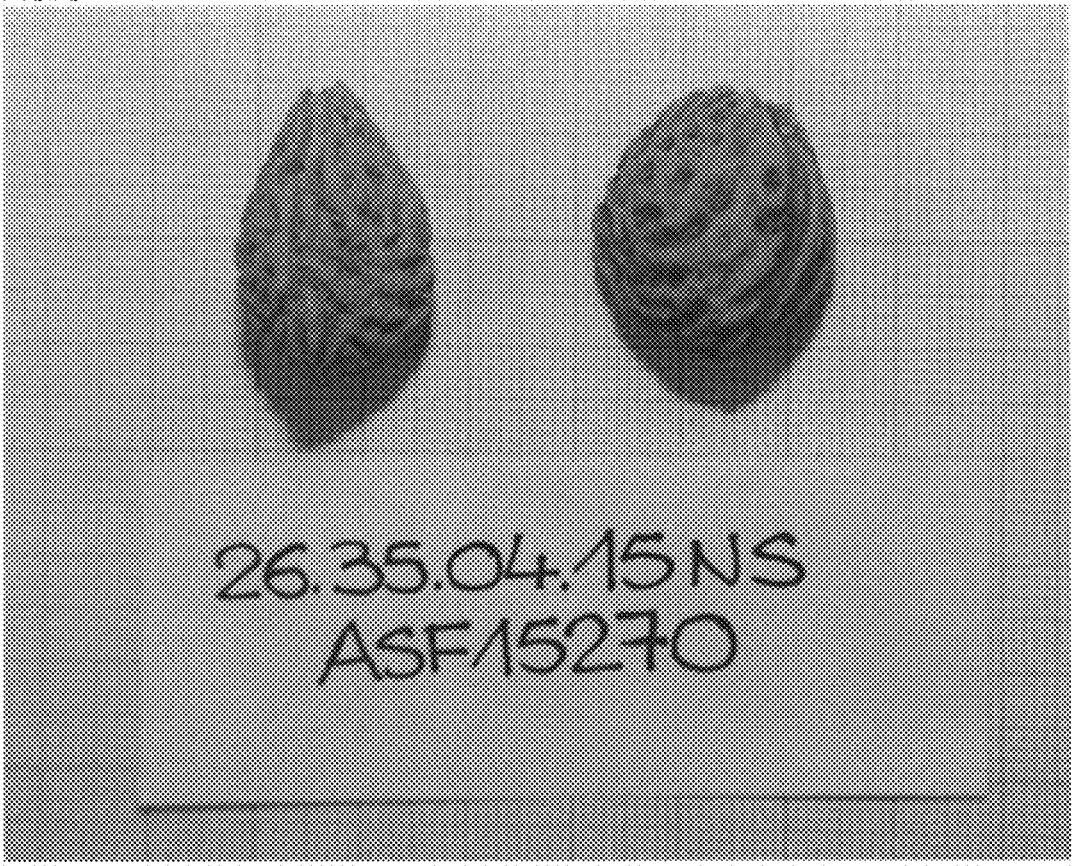
FIG. 6 is a color photograph that show different views of the stone of the new variety.

The views of trees and flowers have been photographed in their third growing season (second year of production). The views of fruits, leaves and stones have been photographed in their second growing season (first year of production).

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'NSRED15270' is high, due to fruit very long shelf life without alteration after harvesting.

Trees are medium vigorous and large stature half-standing in a semi-flared aspect. The anthocyanic coloration of flowering shoot is present excluding brushwood side away from sun. The time of beginning of flowering is considered medium; the flowering usually begins during the first two weeks of March. The type of flower is showy (rosette) with medium petal size. Petals are colored in pink. Leaf glands are present and round. The fruit flesh is red, also named blood red. The fruit skin is medium thick, with a homogenous and dark purple red color on a red background. The stone is semi clingstone and its size is medium. Fruit taste is semi-sweet, very aromatic and with a high level of sugars.

Compared to 'NECTARPERF' white nectarine tree (U.S. Plant Pat. No. 23,357), which is the seed parent of 'NSRED15270', the new variety shows a surprising bright blood dark red flesh color whereas the fruits of 'NECTARPERF' present a white colored flesh.

The ripening time of the new variety 'NSRED15270' is considered medium to late, namely at the end of July or early in August, whereas the fruits of the variety 'NECTARPERF' ripen late during the season, namely at the end of August or early in September depending on the years.

Compared to 'NSRED15268' blood nectarine tree (U.S. Plant patent application Ser. No. 16/350,457), the fruits of the variety named 'NSRED15270' usually ripen at least 5 to 10 days later. Thus, the variety 'NSRED15270' has a later time of fruit maturity, in comparison with the similar variety named 'NSRED15268'.

The fruits of the 'NSRED15268' variety are considered rounder than those of the 'NSRED15270' variety, which are considered round to slightly triangular in shape.

The flowers of the 'NSRED15270' variety are medium in size, whereas the flower size of the variety 'NSRED15268' is considered medium to large. Thus, the flowers of 'NSRED15270' are smaller than the flowers of the similar variety 'NSRED15268'.

DETAILED DESCRIPTION

Referring more specifically to the pomological details of this new and distinct variety of red nectarine tree, the following was observed on trees in their second growing season (first year of production) for fruits, leaves and stones and on trees in their third growing season (second year of production) for the trees, flowers and trunk, under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. (Royal Horticultural Society) Color Chart (Fourth Edition) provided by The Royal Horticultural Society of Great Britain.

Tree:

*Size.*—

*Generally.*—Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduced to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium vigorous.

*Productivity.*—The productivity is considered good and regular, every year. Fruit set is spaced by thinning to develop the remaining fruit into the desired market sized fruit. The number of the fruit set varies with the prevailing climatic conditions and cultural practices employed during the bloom period and is therefore not distinctive of the present variety.

*Bearer*.—Very regular. The fruit distribution is considered homogenous on mixed branches and spurs having more than 1 year. Thinning of 1 fruit out of 3 was necessary for the tree valorisation. Thinning was necessary every year during the years of observation.

*Form*.—The 'NSRED15270' variety has naturally a semi-flared shape.

*Density*.—Considered dense.

*Hardiness*.—The present tree was grown and evaluated in France. The variety appears to be hardy under the central Pyrénées-Orientales departement typical climatic conditions. Experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017 and 1017 hours in 2017-2018 showed a good behaviour of the trees in all cases. No damages were caused by ascertained temperatures as low as −12 degrees Celsius in winter. The tree was also very resistant to frosty springtime weather.

Trunk:

*Diameter*.—Approximately 72.0 to 78.0 millimeters in diameter when measured at a distance of approximately 20.0 centimeters above the soil level on the 3$^{rd}$ growing season.

*Bark texture*.—Considered rough, with lenticels.

*Lenticels*.—Numerous lenticels are present. The number of lenticels reaches 2 lenticels per cm$^2$. The lenticels range in size approximately 1.5 to 2.0 millimeters in height and from approximately 5.0 to 6.0 millimeters in width.

*Lenticel color*.—The lenticels have a light orange color (RHS Greyed Orange 165 B).

*Bark coloration*.—The bark has a light brown (RHS Greyed Orange 165 A) color.

Branches:

*Size*.—Mature branches and current season shoots are considered medium for the variety.

*Diameter*.—Average as compared to other nectarine varieties. The current season shoots have a diameter of approximately 4.0 to 6.0 millimeters, and branches in their second growing season have a diameter from 8.0 to 10.0 millimeters.

*Surface texture*.—Average, wood which is several years old has no furrowed appearance.

*Crotch angles*.—Primary branches are considered variable, but the crotch angles are generally of 75 degrees for the current season shoots and 55 degrees for the mature branches from the horizontal axis. This particular characteristic is not considered distinctive of the variety, however.

*Internode length*.—Generally between 22.0 and 28.0 millimeters for the current season shoots and between 26.0 and 32.0 millimeters for the mature branches.

*Current seasons shoots*.—

*Color*.—The color of new shoot tips is considered green (RHS Yellow Green 145 A) on lower part of new shoot tips, whereas the upper part is darker and colored in purple-brown (RHS Greyed Red 178 A).

*Surface texture*.—Smooth, without lenticel.

*Mature branches*.—

*Color of mature branches*.—Brown (RHS Grey Brown 199 A).

*Surface texture*.—The surface texture of mature branches is rough, with small lenticels.

*Lenticels*.—The number of lenticels on mature branches reaches 5 lenticels per cm$^2$. The lenticels range in size approximately 0.5 millimeter in height and approximately 1.5 to 2.0 millimeters in width. The lenticels are stretched round in shape.

*Lenticel color*.—The lenticels on mature branches have a beige color (RHS Greyed Orange 164 C to RHS Greyed Orange 164 D).

Leaves:

*Size*.—Considered medium for the species.

*Leaf length*.—Approximately 174.5 millimeters with leaf petiole.

*Leaf width*.—Approximately 49.75 millimeters.

*Leaf base shape*.—Concave.

*Leaf form*.—Lanceolate.

*Leaf tip form*.—Acute.

*Leaf base form*.—Acute.

*Leaf thickness*.—Medium.

*Leaf color*.—

*Upper leaf surface*.—Green (RHS Yellow Green 147 A).

*Lower surface*.—A lighter green (RHS Yellow Green 147 B) than the upper leaf surface color.

*Leaf texture*.—Smooth and glabrous on both surfaces.

*Leaf venation*.—Pinnately veined.

*Mid-vein*.—

*Color*.—The mid-vein or midrib is light green (RHS Yellow Green 145 C). The color may evolve with maturity.

*Thickness*.—Approximately 1.5 millimeters.

*Lateral veins*.—

*Color*.—The lateral veins are considered a light green (RHS Yellow Green 145 C) similar to the midrib color.

*Leaf margins*.—Crenate.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Shape*.—Ribbed.

*Length*.—About 11.0 to about 14.0 millimeters.

*Diameter*.—About 1.7 to 2.0 millimeters.

*Petiole color*.—

*Upper petiole surface*.—Green (RHS Yellow Green 144 A to RHS Yellow Green 144 B).

*Lower surface*.—Light green (RHS Yellow Green 145 A to RHS Yellow Green 145 B).

*Leaf glands*.—

*Size*.—Considered medium. Their length is about 1.0 millimeter and their width is about 1.0 millimeter.

*Number*.—Generally 2 glands per leaf.

*Type*.—Round.

*Color*.—On older leaves, leaf glands color turns to a brown color (RHS Brown 200 B).

*Margins*.—Smooth and regular

*Leaf stipules*.—

*Generally*.—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are round in form with a round tip. Their form is evolving until blooming, with variables dimensions. Just before blooming, floral buds are approximately 8.0 to 10.0 millimeters wide and approximately 16.0 to 18.0 millimeters long. The distribution of the flower buds is considered homogenous on the trees.

*Color.*—This characteristic is dependent upon the proximity to bloom. At pre-floral stage of development (stage A), the bottom of the flowers buds, or calyx, or flower receptacle, is of purple-brown color at the outer surface of the calyx (RHS Greyed Purple 187 A to RHS Greyed Purple 187 B). The inner surface of the calyx is considered orange yellow (RHS Yellow Orange 23 A) The corolla, formed by the petals, is generally of pink color (RHS Red Purple 65 A to RHS Red Purple 65 B). Petal and sepal color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins during the first two weeks in March. The first bloom was observed on Mar. 13, 2016.

*Blooming time.*—Considered medium-season in relative comparison to other commercial nectarine cultivars grown in the Pyrénées-Orientales departement, France. The date of full bloom is observed at the middle of the blooming period. The date of bloom varies slightly with climatic conditions and cultural practices. Thus, the first full bloom was observed from March 13$^{th}$ until Mar. 21, 2016, then from March 6$^{th}$ until Mar. 13, 2017.

*Duration of bloom.*—Approximately 8 to 9 days. This characteristic varies slightly with the prevailing climatic conditions.

*Flower type.*—The variety is considered to have a showy type flower (rosette type).

*Flower size.*—Considered medium. Flower diameter at full bloom is approximately 38.0 to 42.0 millimeters.

*Bloom quantity.*—Considered abundant, approximately between 35 and 40 flowers per meter, with a good distribution and a high rate of fruit set.

*Flower bud frequency.*—Generally 2 flower buds appear per node, occasionally 1.

*Petal size.*—

*Generally.*—Considered medium.

*Length.*—Generally between 18.0 to 19.0 millimeters.

*Width.*—Generally 18.0 to 19.0 millimeters.

*Petal form.*—Round-shaped.

*Petal count.*—Generally 5.

*Petal texture.*—Smooth.

*Arrangements of petals.*—Overlapping.

*Petal color.*—Both surfaces of the petal are colored in pink (RHS Red purple 65 A to RHS Red Purple 65 B) when young, becoming slightly darker until the end of blooming.

*Fragrance.*—Moderate.

*Petal claw.*—

*Form.*—The claw is considered to be narrower at the base.

*Length.*—Approximately 1.5 to 2.0 millimeters.

*Width.*—Approximately 1.5 millimeters at the base.

*Color.*—A darker pink (RHS Red Purple 63 A) than the petal color.

*Petal margins.*—Generally considered slightly undulating.

*Petal apex.*—

*Generally.*—The petal apices are generally wide-dome shaped.

*Flower pedicel.*—

*Length.*—Considered medium and having an average length of approximately 2.5 to 3.5 millimeters.

*Diameter.*—Considered average, approximately 1.5 to 2.0 millimeters.

*Color.*—Green (RHS Yellow Green 144 A to RHS Yellow Green 144 B).

*Calyx.*—

*Internal surface texture.*—Smooth.

*Color.*—At the stage F of blooming, when the flower is open, the inner surface of the calyx, or flower receptacle, is matt and considered yellow orange (RHS Yellow Orange 16 A). The outer surface of the calyx is considered of purple-brown color (RHS Greyed Purple 187 A or RHS Greyed Purple 187 B).

*Sepals.*—

*Number.*—Generally five sepals.

*Shape.*—Conic with a round tip.

*Surface texture.*—The outer surface has a short, fine pubescent texture.

*Margins.*—Smooth.

*Size.*—Medium.

*Length.*—Approximately 5.0 to 6.0 millimeters.

*Width.*—Approximately 4.0 to 5.0 millimeters.

*Color.*—At the stage F of blooming, the lower surface of the sepals is greenish (RHS Yellow Green 146 A to RHS Yellow Green 146 B). The upper surface of sepals is colored with a purple-brown (RHS Greyed Purple 187 A to RHS Greyed Purple 187 B).

*Average number of stamens per flower.*—Approximately 29 to 34 stamens per flower.

*Anthers.*—

*Generally.*—Medium in length, with a cordate shape.

*Color.*—Red color (RHS Red 42 A to RHS Red 42 B) to yellow color (RHS Yellow 11 B) depending on the maturity stage.

*Pollen production.*—Pollen production is considered medium and the pollen shows a yellow color (RHS Yellow 8 A to RHS Yellow 8 B) which may evolve with maturity. The present variety is considered auto-fertile (self-pollinating).

*Filaments.*—

*Size.*—Medium length, between 11.0 and 14.0 millimeters in length. Filaments length is generally smaller than the pistil's length when not equal to the pistil's length.

*Color.*—Considered white (RHS White N155 D) to light pink (RHS Red Purple 63 C) depending on the maturity stage. The color evolves and becomes darker during the blooming.

*Pistil.*—

*Number.*—Usually 1.

*Generally.*—Average in size.

*Length.*—Approximately 17.0 to 19.0 millimeters including the ovary. Generally higher than stamen length.

*Color.*—Considered green (RHS Yellow Green 145 A to RHS Yellow Green 145 B) to yellowish (RHS Yellow Green 153 B to RHS Yellow Green 153 C) depending on the maturity stage.

*Stigma.*—Approximately 1.0 millimeter in diameter, with a yellowish color (RHS Yellow Green 153 B to RHS Yellow Green 153 C).

*Ovary.*—Approximately 2.0 to 2.5 millimeters in height. The diameter of the ovary is about 1.5 to 2.0 millimeters. The color is considered green (RHS Yellow Green N144 A to RHS Yellow Green N144 B).

Fruit:

*Maturity when described.*—Very firm in ripe conditions (shipping ripe).

*Date of first picking.*—Jul. 24, 2015.

*Date of last picking.*—The date of harvest varies slightly with the prevailing climatic conditions. The 'NSRED15270' variety has a medium to late date of picking, and a grouped maturity. The maturity is grouped within 6 to 8 days and the harvest is generally performed in two runs. Last known picking times carry on from July 24$^{th}$ to Jul. 31, 2015, then from July 28$^{th}$ to Aug. 4, 2016, then from July 24$^{th}$ to Jul. 29, 2017, and then from July 20$^{th}$ to Jul. 28, 2018.

*Size.*—

*Generally.*—Homogeneous in size. Generally 2A.

*Average cheek diameter.*—Approximately 69.0 to 72.0 millimeters.

*Average axial diameter.*—Approximately 63.0 to 65.0 millimeters.

*Typical weight.*—Generally about 168.0 grams. This characteristic is high dependent upon the prevailing cultural practices, and therefore is not particularly distinctive of the variety.

*Fruit form.*—

*Generally.*—Round to slightly triangular.

*Fruit suture.*—Wide-mouthed and slightly marked, extending from the base to the apex. No apparent callousing or stitching exists along the suture line. Not pointed.

*Mucron.*—Absent.

*Suture.*—

*Color.*—The suture has generally a similar dark red color to the whole fruit color (RHS Greyed Purple N 186 A to RHS Greyed Purple N 186 B).

*Ventral surface.*—

*Form.*—Smooth.

*Apex.*—Non-prominent, generally slightly depressed.

*Base.*—Semi-flared, shallow.

*Stem cavity.*—Flared. The depth of the stem cavity is considered medium, between 13.0 and 15.0 millimeters. Average width is about 17.0 to 20.0 millimeters.

*Fruit skin.*—

*Thickness.*—Considered medium thick and strong, and the adherence of skin to flesh is strong to medium, depending on the fruit maturity.

*Texture.*—Smooth and glabrous, without any pubescence, and with few bumps.

*Taste.*—Semi-sweet.

*Tendency to crack.*—None observed.

*Color.*—

*Blush color.*—This blush color is dark purple red (RHS Greyed Purple N186 A to RHS Greyed Purple N186 B). The red blush covers almost 100% of the fruit skin surface on a purple red (RHS Greyed Purple 187 A) background. The percentage of the blush on the fruit skin surface can vary and is generally dependant upon the prevailing conditions under which the fruit was grown.

*Ground color.*—The ground color covers at the most 5% of the fruit skin surface, and is considered purple red (RHS Greyed Purple 187 A).

*Lenticels.*—No lenticel is present on the skin surface.

*Fruit stem.*—Medium in length, approximately 9.0 to 11.0 millimeters.

*Diameter.*—Approximately 4.0 to 5.0 millimeters.

*Color.*—Pale green (RHS Yellow Green 145 A).

*Flesh.*—

*Ripens.*—Very homogenously, slowly. The flesh has a long shelf life.

*Texture.*—Very firm, very dense, crunchy, melting, juicy at harvest maturity stage.

*Fibers.*—Not fibrous.

*Aroma.*—Pronounced.

*Eating quality.*—Considered very good and aromatic.

*Flavor.*—Considered semi-sweet, sugary and very aromatic. The Brix is generally superior to 12 and acidity comprised between 6 and 9 meq/100 ml.

*Juice.*—Very juicy at complete maturity.

*Brix.*—Generally 12.9 degrees. This characteristic varies slightly with the number of fruit per tree; prevailing cultural practices; and the surrounding climatic conditions.

*Flesh color.*—The flesh of the new variety 'NSRED15270' is colored in a dark red (RHS Greyed Purple 185 A), also named blood red color. Usually, the color is identical, i.e. dark red, around the stone cavity (no white circle is observed around the cavity).

Stone:

*Type.*—Semi clingstone, more or less adherent depending on the fruit maturity.

*Size.*—Considered medium for the variety. The stone size varies significantly depending upon the tree vigor, crop load and prevailing growing conditions.

*Length.*—Approximately 25.0 to 28.0 millimeters.

*Width.*—Approximately 21.0 to 22.0 millimeters.

*Diameter.*—Approximately 17.0 to 18.0 millimeters.

*Form.*—Obovate.

*Base.*—Straight.

*Apex.*—

*Shape.*—The stone apex is short.

*Stone cavity*.—Considered medium size, with a form and dimensions corresponding to the stone's dimensions.

*Stone surface*.—

*Surface texture*.—The pit is transversely furrowed on its entire surface. Furrows are more pronounced toward the apex. The stone is pitted toward the base. Relief is prominent generally and present basally.

*Ridges*.—The surface texture is generally characterized by more prominent ridges along the ventral edges and is more prominent at the apical tip.

*Ventral edge*.—

*Width*.—Considered small, and having a dimension of approximately 2.0 millimeters at mid-suture.

*Dorsal edge*.—

*Shape*.—Grooved.

*Stone color*.—The color of the dry stone is generally considered light brown (RHS Greyed Orange 165 B to RHS Greyed Orange 165 C).

*Tendency to split*.—Splitting is absent, depending on climatic conditions between blooming period and stone hardening.

*Kernel*.—

*Size*.—The kernel is considered medium.

*Length*.—Approximately 8.0 millimeters.

*Width*.—Approximately 6.0 millimeters.

*Thickness*.—Approximately 4.0 millimeters.

*Form*.—Obovate.

*Pellicle*.—The pellicle of the kernel has a short pubescence.

*Color*.—The kernel skin is a light brown color (RHS Greyed Orange 164 A). The almond, which is the seed of the kernel, is white (RHS White 155 D) and has a bitter tasting. The kernel and its embryo are mature at the time of fruit maturity.

*Use*.—The subject variety 'NSRED15270' is considered to be a nectarine tree having a medium to late season of fruit maturity, and which produces fruits that are considered firm, attractively colored with a very dark purple red. The high content of antioxidant in the red flesh convert fruits in a very healthy product. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality*.—Considered very good. The fruit of the new red blood nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease*.—No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

The invention claimed is:

1. A new and distinct variety of red blood nectarine tree as illustrated and described, characterized by fruits with high eating quality and very long shelf life without alteration before and after harvesting, with a semi-sweet red blood colored flesh, and a very high percentage of dark purple red blush on skin surface.

* * * * *